(12) United States Patent
Peltier

(10) Patent No.: US 9,261,439 B2
(45) Date of Patent: Feb. 16, 2016

(54) CELL DEPOSITION SYSTEM

(75) Inventor: Eric Roger Louis Peltier, Clamart (FR)

(73) Assignee: NOVACYT, Velizy Villacoublay (FR)

( * ) Notice: Subject to any disclaimer, the term of this patent is extended or adjusted under 35 U.S.C. 154(b) by 702 days.

(21) Appl. No.: 13/357,868

(22) Filed: Jan. 25, 2012

(65) Prior Publication Data

US 2012/0122142 A1 May 17, 2012

Related U.S. Application Data

(62) Division of application No. 12/375,784, filed as application No. PCT/FR2007/001066 on Jun. 26, 2007, now abandoned.

(30) Foreign Application Priority Data

Jul. 31, 2006 (FR) ...................................... 06 07005

(51) Int. Cl.
*C12M 1/34* (2006.01)
*C12M 3/00* (2006.01)
*G01N 1/28* (2006.01)
*B01L 3/00* (2006.01)

(52) U.S. Cl.
CPC .............. *G01N 1/2813* (2013.01); *B01L 3/502* (2013.01); *B01L 2200/0621* (2013.01); *B01L 2200/0668* (2013.01); *B01L 2300/069* (2013.01); *B01L 2400/0633* (2013.01); *G01N 2001/2826* (2013.01); *G01N 2001/2846* (2013.01)

(58) Field of Classification Search
CPC ................ B01L 2200/0621; B01L 2200/0668; B01L 2300/069; B01L 2400/0633; B01L 3/502; G01N 1/2813; G01N 2001/2826; G01N 2001/2846

USPC ............. 435/287.7, 287.9, 307.1; 422/72, 81, 422/82, 501, 551; 436/45, 46
See application file for complete search history.

(56) References Cited

U.S. PATENT DOCUMENTS

| 5,318,749 A | 6/1994 | Eberle |
| 5,732,287 A | 3/1998 | Morse |
| 5,840,584 A | 11/1998 | Waldenburg |
| 6,627,158 B1 | 9/2003 | Peltier |

FOREIGN PATENT DOCUMENTS

| DE | 84 16 418 | 8/1984 |
| DE | 39 36 093 | 5/1990 |
| EP | 1 045 249 | 10/2000 |
| FR | 2 869 413 | 10/2005 |

OTHER PUBLICATIONS

International Search Report dated Nov. 13, 2007 corresponding PCT application No. PCT/FR2007/001066.

*Primary Examiner* — Michael Marcheschi
*Assistant Examiner* — Shanta G Doe
(74) *Attorney, Agent, or Firm* — Young & Thompson

(57) ABSTRACT

A system for depositing cells on an analysis plate, the cells being contained in a cell suspension including a fixing agent and the cells, included, for receiving the suspension, a chamber (5) which is positioned above the analysis plate and whose base is open and extends opposite a cell depositing zone of the plate and a material for absorbing the fixing agent placed around the chamber and the depositing zone of the plate. The chamber is mounted so as to be able to be moved between a first position in abutment against the analysis plate in order to allow the cells to be deposited on the depositing zone of the plate via decantation and a second position remote from this analysis plate in order to place the chamber in a fluid relationship with the absorption material in order to allow this material to absorb the fixing agent.

5 Claims, 2 Drawing Sheets

CELL DEPOSITION SYSTEM

CROSS REFERENCE TO RELATED APPLICATIONS

This application is a division of application Ser. No. 12/375,784 filed on May 5, 2009, now abandoned; which is the 35 U.S.C. 371 national stage of International application PCT/FR07/001066 filed on Jun. 26, 2007; which claims priority to French application 0607005 filed on Jul. 31, 2006. The entire contents of each of the above-identified applications are hereby incorporated by reference.

BACKGROUND OF THE INVENTION

The present invention relates to a system for depositing cells on an analysis plate.

In order to screen or diagnose lesions, cell samples are taken and are placed in suspension so that they can be analysed.

Generally, these samples can be taken using specific brushes, needles or any other appropriate means and are then introduced into a bottle containing a cell fixing agent so that the cells which have been removed are fixed by the fixing agent and form a suspension therewith.

The cells must then be deposited on an analysis plate.

Various deposition methods and systems for this type of application are already known from the prior art.

In this manner, for example, centrifuging means and filtering means have been used to obtain this cell deposit on the plate.

However, such means are relatively complex, bulky, costly and are not very easy to use.

The deposit of the cells can also be obtained by means of a simple decantation operation.

In this instance, the cell suspension comprising the cell fixing agent and the cells is poured into a receiving chamber which is positioned above the analysis plate and whose base is open and extends opposite a cell depositing zone of the analysis plate.

The cells are deposited progressively on the plate, then the fixing agent is withdrawn from the chamber.

However, it will be appreciated that this operation which involves removing the fixing agent without moving the cells is very long and complex.

In order to overcome these problems, document FR-A-2 792 333 proposes a system for depositing cells on an analysis plate, the cells being contained in a cell suspension which comprises a cell fixing agent and the cells, the suspension being poured into a receiving chamber which is positioned above the analysis plate and whose base is open and extends opposite a cell depositing zone of the analysis plate. According to this system, the base of the chamber is in fluid communication with a material for absorbing the fixing agent in order to progressively absorb it and to allow a homogeneous deposit of the cells on the cell depositing zone of the analysis plate.

When used, however, such a system also had a given number of disadvantages, in particular with respect to the time required for the absorption of the fixing agent and therefore the deposit of the cells on the analysis plate.

The object of the invention is therefore to overcome these problems.

SUMMARY OF THE INVENTION

To this end, the invention relates to a system for depositing cells on an analysis plate, the cells being contained in a cell suspension comprising a fixing agent and the cells, comprising, for receiving the suspension, a chamber which is positioned above the analysis plate and whose base is open and extends opposite a cell depositing zone of the plate and a material for absorbing the fixing agent placed around the chamber and the depositing zone of the plate, characterised in that the chamber is mounted so as to be able to be moved between a first position in abutment against the analysis plate in order to allow the cells to be deposited on the depositing zone of the plate by means of decantation and a second position remote from this analysis plate in order to place the chamber in a fluid relationship with the absorption material in order to allow this material to absorb the fixing agent.

According to specific embodiments, the system comprises one or more of the following features:
- the base of the chamber is provided with sealing means;
- the chamber is connected to means for moving the chamber between its two positions at the end of a predetermined period of time;
- the predetermined period of time is approximately 30 minutes; and
- the absorption material is in the form of a sheet of absorbent paper which is placed around the depositing zone of the plate and the chamber.

BRIEF DESCRIPTION OF THE DRAWINGS

The invention will be better understood from a reading of the following description, given purely by way of example and with reference to the appended drawings, in which.

Figure 1:
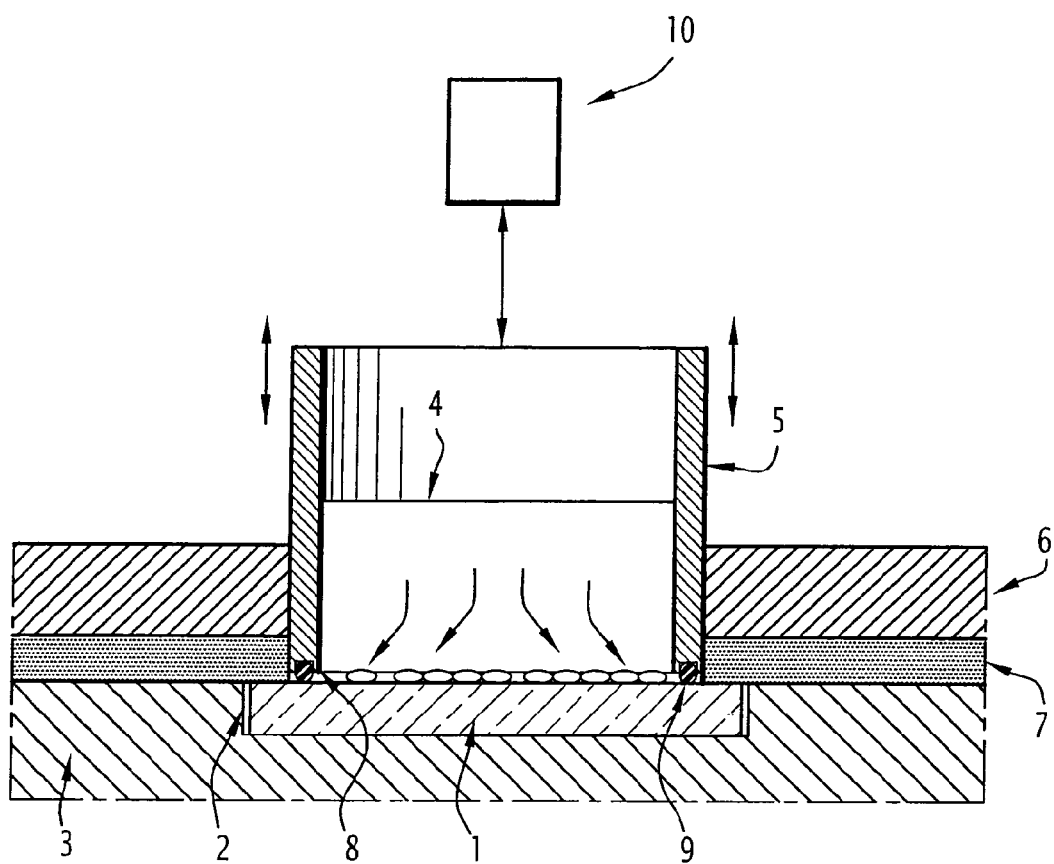
FIG. 1 is a schematic section of a depositing system according to the invention, in which the chamber is in its first position.

These Figures illustrate a system for depositing cells on an analysis plate.

DETAILED DESCRIPTION OF THE INVENTION

The analysis plate is generally designated 1 and is formed by any appropriate plate which is already known from the prior art.

This plate is received in a corresponding recess 2 of a component 3 which forms a base and which will be described in greater detail below.

A cell suspension which is generally designated 4 is poured into a receiving chamber 5 which is placed above the analysis plate and whose base is open and extends opposite a cell depositing zone of the analysis plate.

This receiving chamber 5 is, for example, placed in a support component 6 which will be described in greater detail below and which extends opposite the component which forms a base 3. The depositing system also comprises a material for absorbing the cell fixing agent.

This absorption material is generally designated 7 in these Figures and is, for example, in the form a sheet of absorbent paper which has the thickness of the liquid deposit (approximately 0.5 mm) and which is provided with a hole 8 which is capable of extending opposite the cell depositing zone of the analysis plate.

The absorption material extends around the cell depositing zone of the plate and the receiving chamber 5 and is therefore positioned between the components which form a base 3 and support components 6 around this chamber 5 for receiving the suspension.

These components which form a base and support can be fixed and locked to each other, for example, using fixing means and locking means which allow the sheet of absorption material to be held in position by means of clamping therebetween.

Figure 2:
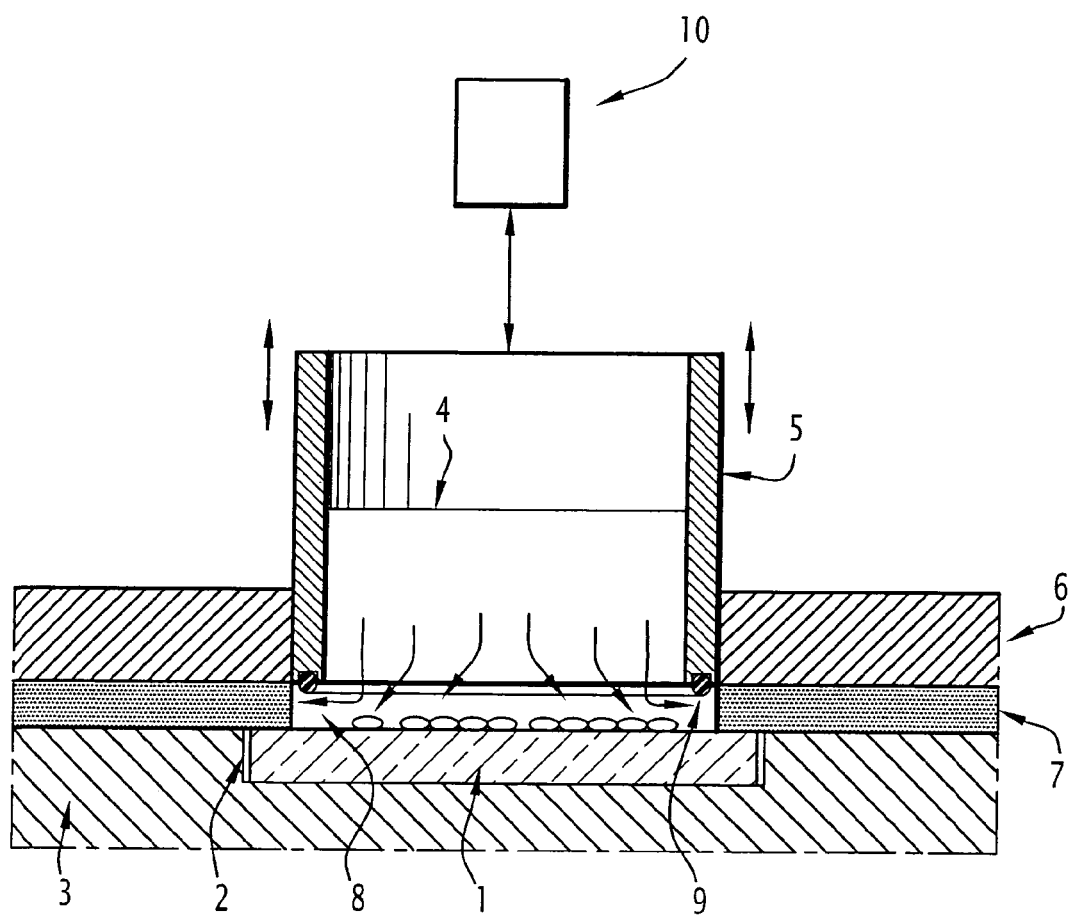
FIG. 2 is a similar view, in which the chamber is in its second position.

It should also be noted that the lower edge of the chamber 5 can be provided, for example, with a sealing joint 9 such as, for example, an O-ring and the chamber can be moved relative to this plate, as illustrated in FIGS. 1 and 2 using means for controlling the movement thereof, generally designated 10.

These control means may have any appropriate structure.

These means allow this chamber to be moved between the position illustrated in FIG. 1, in which the chamber and more particularly the base thereof and the sealing joint are in abutment against the analysis plate, thus preventing the absorption material from absorbing the cell fixing agent of the suspension contained in the chamber.

The chamber is held in this position for a predetermined period of time, for example, of approximately 30 minutes in order to allow a homogeneous deposit by cells being decanted on the analysis plate, as illustrated.

At the end of this predetermined period of time, the control means bring about a movement of the chamber from the position illustrated in FIG. 1 to the position illustrated in FIG. 2, in which this chamber is remote from the analysis plate, thus placing the fixing agent of the cell suspension and the absorption material in a fluid relationship.

Tests have shown that after a period of time of 30 minutes, the cells are already in the correct position and it is possible to initiate the absorption of the fixing agent in order to save time during the depositing operation of the cells on the analysis plate.

Of course, various embodiments of this system may be envisaged, in particular with respect to the movement means and the sealing means of the chamber.

It will be appreciated that this structure allows the cells to be deposited in a rapid and homogeneous manner on the analysis plate, in particular in the form of a single layer, which facilitates their subsequent analysis, and that this structure is particularly well suited to the analysis of cytological suspensions.

The invention claimed is:

1. A method for depositing cells on an analysis plate, comprising the steps of:
   forming a cell suspension comprising a fixing agent and cells to be deposited on an analysis plate;
   pouring the suspension into a chamber positioned above the analysis plate and whose base is open and extends opposite a cell depositing zone of the analysis plate, an absorption material for absorbing the fixing agent being placed around the chamber and the cell depositing zone of the analysis plate;
   decanting the suspension so that the cells are deposited on the cell depositing zone by decantation while the chamber is in a first position abutting the analysis plate in which the chamber; is not in a fluid relationship with the absorption material; and
   after the decanting step, moving the chamber to a second position remote from the analysis plate in which the chamber is in a fluid relationship with the absorption material in order to allow the absorption material to absorb the fixing agent.

2. The method of claim 1, wherein the base of the chamber is provided with sealing means.

3. The method of claim 1, further comprising moving the chamber from the first position to the second position at the end of a predetermined period of time.

4. The method of claim 3, wherein the predetermined period of time is approximately 30 minutes.

5. The method of claim 1, wherein the absorption material is a sheet of absorbent paper which is placed around the cell depositing zone of the analysis plate and the chamber.

* * * * *